United States Patent
Hallen (10) Patent No.: US 11,540,941 B2
(45) Date of Patent: Jan. 3, 2023

(54) ADJUSTABLE SUPPORT SLEEVE FOR SURGICAL INSTRUMENTS

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 236 days.

(21) Appl. No.: 17/115,947

(22) Filed: Dec. 9, 2020

(65) Prior Publication Data

US 2021/0177653 A1    Jun. 17, 2021

Related U.S. Application Data

(60) Provisional application No. 62/946,612, filed on Dec. 11, 2019.

(51) Int. Cl.
| | | |
|---|---|---|
| *A61F 9/007* | (2006.01) | |
| *A61B 90/00* | (2016.01) | |
| *A61F 9/013* | (2006.01) | |

(52) U.S. Cl.
CPC .......... *A61F 9/00736* (2013.01); *A61B 90/08* (2016.02); *A61F 9/0136* (2013.01); *A61B 2090/0811* (2016.02)

(58) Field of Classification Search
CPC .... A61F 9/00736; A61F 9/007; A61F 9/0136; A61B 2090/0811; A61B 90/08; A61M 25/0138; A61M 25/0141; A61M 25/0144; A61M 25/0147; A61M 2025/0161
See application file for complete search history.

(56) References Cited

U.S. PATENT DOCUMENTS

| | | | |
|---|---|---|---|
| 3,805,787 A | 4/1974 | Banko | |
| 4,030,567 A | 6/1977 | Kondo | |
| 5,019,035 A | 5/1991 | Missirlian | |
| 5,114,403 A * | 5/1992 | Clarke | A61M 25/01 |
| | | | 604/95.04 |
| 5,190,050 A | 3/1993 | Nitzsche | |
| 5,217,465 A | 6/1993 | Steppe | |
| 5,370,658 A | 12/1994 | Scheller | |
| 5,396,880 A | 3/1995 | Kagan et al. | |
| 6,312,402 B1 | 11/2001 | Hansmann | |
| 6,575,989 B1 | 6/2003 | Scheller | |

(Continued)

FOREIGN PATENT DOCUMENTS

| | | |
|---|---|---|
| CN | 202426711 U | 9/2012 |
| CN | 207755450 U | 8/2018 |

(Continued)

*Primary Examiner* — Majid Jamialahmadi
(74) *Attorney, Agent, or Firm* — Patterson + Sheridan, LLP (57) ABSTRACT

The present disclosure generally relates to surgical instruments having adjustable stiffness, and more particularly, surgical instruments having adjustable stiffness for ophthalmic surgical procedures. In one embodiment, a surgical instrument includes a probe, a slidable support sleeve, and a rotatable knob. A stiffness level of the probe may be adjusted by rotating the knob, thereby causing linear displacement of the support sleeve along a length of the probe. The knob may further include a dial depicting a series of settings representing different eye sizes and corresponding to preset positions of the support sleeve relative to the probe. Thus, a user may select an optimal stiffness of the probe for a particular eye size by rotating the knob to the corresponding setting.

14 Claims, 4 Drawing Sheets

(56) References Cited

U.S. PATENT DOCUMENTS

| | | |
|---|---|---|
| 6,749,601 B2 | 6/2004 | Chin |
| 6,908,476 B2 | 6/2005 | Jud |
| 6,945,984 B2 | 9/2005 | Arumi |
| 7,207,980 B2 | 4/2007 | Christian |
| 7,338,494 B2 | 3/2008 | Ryan |
| 7,909,816 B2 | 3/2011 | Buzawa |
| 8,038,692 B2 | 10/2011 | Valencia |
| 8,187,293 B2 | 5/2012 | Kirchhevel |
| 8,202,277 B2 | 6/2012 | Ryan |
| 8,308,737 B2 | 11/2012 | Ryan |
| 8,845,666 B2 | 9/2014 | Underwood |
| 8,894,636 B2 | 11/2014 | Gille et al. |
| 9,060,841 B2 | 6/2015 | Mccawley |
| 9,138,346 B2 | 9/2015 | Scheller |
| 9,370,447 B2 | 6/2016 | Mansour |
| 9,585,788 B2 | 3/2017 | Underwood |
| 9,757,274 B2 | 9/2017 | Scheller et al. |
| 9,775,943 B2 | 10/2017 | Scheller |
| 9,795,505 B2 | 10/2017 | Yu et al. |
| 9,925,326 B2 | 3/2018 | Scheller |
| 9,931,244 B2 | 4/2018 | Ryan |
| 9,949,876 B2 | 4/2018 | Mansour |
| 10,045,883 B2 | 8/2018 | Egli |
| 10,085,883 B2 | 10/2018 | Auld |
| 10,179,007 B2 | 1/2019 | Peterson |
| 10,285,583 B2 | 5/2019 | Parto |
| 10,376,315 B2 | 8/2019 | Scheller et al. |
| 10,391,232 B2 | 8/2019 | Scheller et al. |
| 10,413,445 B2 | 9/2019 | Scheller et al. |
| 10,413,446 B2 | 9/2019 | Bouch et al. |
| 10,617,560 B2 | 4/2020 | Ryan |
| 10,639,197 B2 | 5/2020 | Lopez |
| 10,675,181 B2 | 6/2020 | Murakami |
| 10,828,192 B2 | 11/2020 | Scheller et al. |
| 10,898,373 B2 | 1/2021 | Ryan |
| 10,945,872 B2 | 3/2021 | Ryan |
| 11,020,270 B1 | 6/2021 | Peyman |
| 11,278,449 B2 | 3/2022 | Ryan |
| 2003/0195539 A1 | 10/2003 | Attinger |
| 2005/0033309 A1 | 2/2005 | Ryan |
| 2005/0209618 A1 | 9/2005 | Auld |
| 2007/0099149 A1 | 5/2007 | Levy et al. |
| 2007/0106300 A1 | 5/2007 | Auld |
| 2007/0255196 A1 | 11/2007 | Wuchinich |
| 2008/0195135 A1 | 8/2008 | Attinger |
| 2008/0255526 A1 | 10/2008 | Bosse et al. |
| 2009/0093800 A1 | 4/2009 | Auld |
| 2009/0131870 A1 | 5/2009 | Fiser |
| 2010/0063359 A1 | 3/2010 | Okoniewski |
| 2010/0228226 A1 | 9/2010 | Nielsen |
| 2012/0116361 A1 | 5/2012 | Hanlon et al. |
| 2013/0090531 A1 | 4/2013 | Ryan |
| 2013/0090635 A1 | 4/2013 | Mansour |
| 2013/0281817 A1 | 10/2013 | Schaller |
| 2014/0121469 A1 | 5/2014 | Meckel et al. |
| 2014/0128896 A1 | 5/2014 | Ryan |
| 2015/0231687 A1 | 8/2015 | Ookubo et al. |
| 2017/0215855 A1 | 8/2017 | Nunan |
| 2017/0333251 A1 | 11/2017 | Scheller et al. |
| 2018/0214307 A1 | 8/2018 | Ryan |
| 2018/0228651 A1 | 8/2018 | Mansour |
| 2018/0250164 A1 | 9/2018 | Ryan |
| 2018/0360660 A1 | 12/2018 | Lopez |
| 2019/0059936 A1 | 2/2019 | Ryan |
| 2019/0269556 A1 | 9/2019 | Meckel |
| 2019/0282322 A1 | 9/2019 | Mirsepassi |
| 2020/0163717 A1 | 5/2020 | Hartkopf-ceylan |
| 2020/0197217 A1 | 6/2020 | Ryan |
| 2021/0177652 A1 | 6/2021 | Chen et al. |
| 2021/0177653 A1 | 6/2021 | Hallen |
| 2021/0244567 A1 | 8/2021 | Ryan |
| 2021/0251805 A1 | 8/2021 | Ryan |
| 2021/0290438 A1 | 9/2021 | Hallen |
| 2022/0031509 A1 | 2/2022 | Tazawa |
| 2022/0192706 A1 | 6/2022 | Grueebler et al. |

FOREIGN PATENT DOCUMENTS

| | | |
|---|---|---|
| DE | 651436 C | 10/1937 |
| EP | 1955684 A1 | 8/2008 |
| EP | 2760400 B1 | 1/2018 |
| EP | 3319564 B1 | 11/2019 |
| EP | 3191161 B1 | 1/2020 |
| EP | 3656332 A1 | 5/2020 |
| EP | 3352682 B1 | 7/2020 |
| EP | 3332756 B1 | 8/2020 |
| GB | 1448129 A | 9/1976 |
| JP | 2009072221 A | 4/2009 |
| JP | 2020044289 A | 3/2020 |
| JP | 2022040303 A | 3/2022 |
| WO | 0119255 A1 | 3/2001 |
| WO | 2010064670 A1 | 6/2010 |
| WO | 2013133712 A1 | 9/2013 |
| WO | 2017053832 A1 | 3/2017 |
| WO | 2017075514 A1 | 5/2017 |

* cited by examiner

ADJUSTABLE SUPPORT SLEEVE FOR SURGICAL INSTRUMENTS

PRIORITY CLAIM

This application claims the benefit of priority of U.S. Provisional Patent Application Ser. No. 62/946,612 titled "ADJUSTABLE SUPPORT SLEEVE FOR SURGICAL INSTRUMENTS," filed on Dec. 11, 2019, whose inventor is Paul R. Hallen, which is hereby incorporated by reference in its entirety as though fully and completely set forth herein.

BACKGROUND

Field

Embodiments of the present disclosure generally relate to instrumentation for surgical procedures, and more particularly, ophthalmic surgical instrumentation having an adjustable support sleeve.

Description of the Related Art

Continuous efforts to minimize the invasiveness of surgical procedures, such as ophthalmic surgical procedures, have led to the development of small-gauge surgical instrumentation for micro-incision techniques. Small gauge vitrectomy, also known as micro-incision vitrectomy surgery (MIVS), is a classic example of one such type of surgical procedure utilizing small-gauge instrumentation. Examples of common ocular conditions that may be treated by minimally invasive surgery include retinal detachment, macular holes, premacular fibrosis, and vitreous hemorrhages. The benefits associated with modern MIVS as compared to more invasive vitrectomies include access to greater pathology, greater fluidic stability, increased patient comfort, less conjunctival scarring, less postoperative inflammation, and earlier visual recovery, among others. Accordingly, indications for MIVS and other microincision techniques have expanded in recent years.

Despite the aforementioned benefits of microincision techniques and their widespread acceptance, there remain numerous challenges with the utilization of small-gauge surgical instruments, particularly in the field of ophthalmology. One commonly noted concern among ophthalmologists is stiffness of the instrument shaft. The smaller diameter of microincision instrument shafts, such as vitrectomy probes, causes decreased rigidity thereof, making it difficult for surgeons to control the instruments when working with the different types of ocular tissues. Furthermore, different shapes and sizes of patients' eyes require different levels of support for the shaft, and thus surgeons must have available instruments with differing levels of shaft-supporting structures despite having the same gauge. For example, pediatric eyes may be very small compared to adult eyes, and therefore, require the utilization of surgical instruments with increased shaft support.

Accordingly, what is needed in the art are improved small-gauge surgical instruments with adjustable shaft-supporting structures.

SUMMARY

The present disclosure generally relates to surgical instruments having adjustable stiffness, and more particularly, surgical instruments having adjustable stiffness for ophthalmic surgical procedures.

In one embodiment, a surgical instrument is provided. The surgical instrument includes a base unit configured to be held by a user, a probe, a support sleeve slidably coupled to and substantially surrounding a portion of the probe, a linear actuator, and a rotatable knob coupled to the linear actuator. The probe and the support sleeve are disposed through an opening in a distal end of the base unit and extend therefrom. The probe further includes a length parallel to a longitudinal axis thereof. The linear actuator is coupled to the support sleeve within the base unit and is configured to linearly displace the support sleeve along the length of the probe. Rotation of the knob causes rotation of the linear actuator, which in turn causes linear displacement of the support sleeve along the length of the probe.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to surgical instruments having adjustable stiffness, and more particularly, surgical instruments having adjustable stiffness for ophthalmic surgical procedures. In one embodiment, a surgical instrument includes a probe, a slidable support sleeve, and a rotatable knob. A stiffness level of the probe may be adjusted by rotating the knob, thereby causing linear displacement of the support sleeve along a length of the probe. The knob may further include a dial depicting a series of settings representing different eye sizes and corresponding to preset positions of the support sleeve relative to the probe. Thus, a user may select an optimal stiffness of the probe for a particular eye size by rotating the knob to the corresponding setting.

Figure 1:
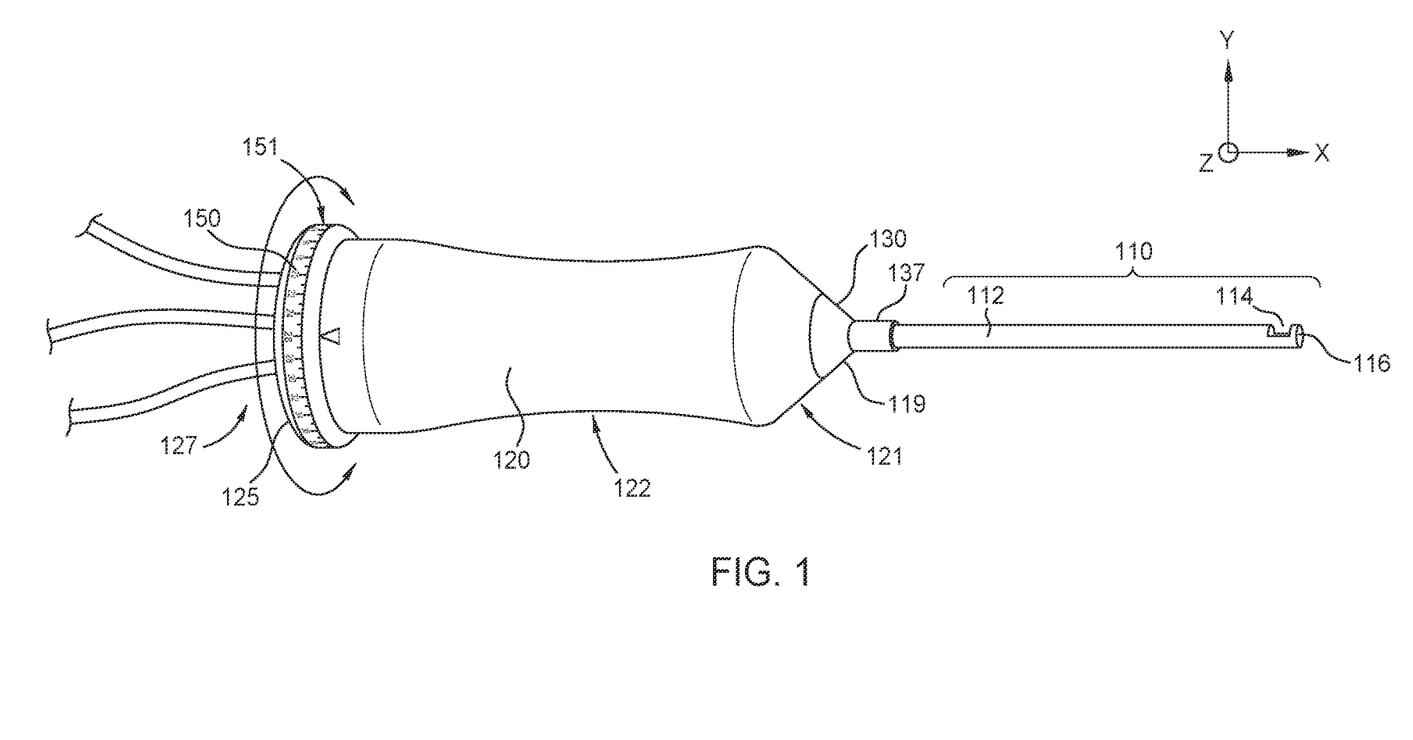
FIG. 1 illustrates a perspective view of an exemplary instrument according to one embodiment of the present disclosure.
Figure 2A:
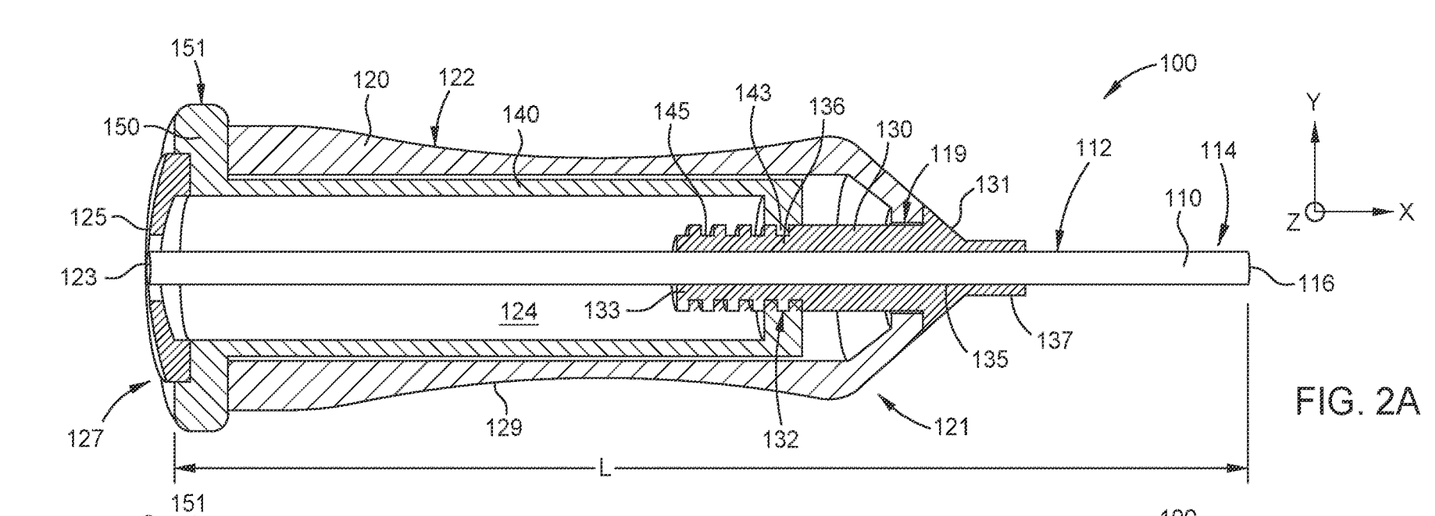
FIG. 2A illustrates a schematic cross-sectional side view of the instrument of FIG. 1 according to one embodiment of the present disclosure.
Figure 2B:
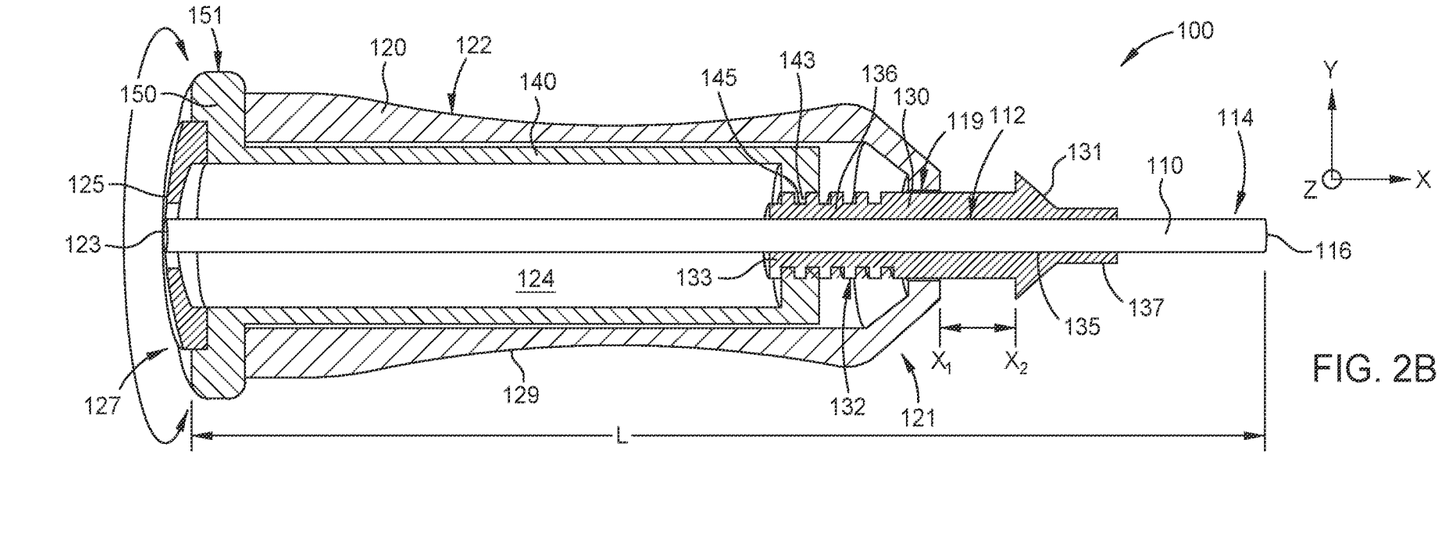
FIG. 2B illustrates a schematic cross-sectional side view of an exemplary instrument according to one embodiment of the present disclosure.

FIG. 1 illustrates a perspective view of an exemplary surgical instrument 100 having an adjustable support sleeve 130 according to one embodiment described herein. FIGS. 2A and 2B illustrate schematic cross-sectional views of the surgical instrument 100 with the support sleeve 130 adjusted to different positions along a length L of a probe 110. Accordingly, FIGS. 1, 2A, and 2B are herein described together for clarity.

The surgical instrument 100 comprises a probe or needle 110 (referred to hereinafter as a "probe") extending into a base unit 120. Generally, the probe 110 is formed of a material suitable for ophthalmic surgical procedures, such as vitreoretinal surgeries that involve removal of the vitreous in the eye, or other surgical procedures. For example, the probe 110 is formed of surgical grade stainless steel, aluminum, or titanium.

The probe 110 includes a proximal portion 112 and a distal portion 114 terminating distally at the distal end 116 exterior to the base unit 120. In some embodiments, the proximal portion 112 extends through a substantial portion of an interior chamber 124 (shown in FIGS. 2A and 2B) of the base unit 120. In one example, the probe 110 is an elongated cutting member of a vitrectomy probe. For example, the probe 110 may be inserted into a cannula for performance of vitreous surgery, which may be aspirating or non-aspirating. Accordingly, the probe 110 may comprise a hollow tube having a diameter less than about 20 gauge. The probe 110 itself may have a diameter less than about 23 gauge, such as a diameter less than about 25 gauge. In one embodiment, the probe 110 has a diameter of approximately 27 gauge. In further examples, the probe 110 may include an illumination device, a laser guide, a suction device, forceps, scissors, retractors, or other suitable devices disposed therein or coupled thereto. Although the instrument 100 is described as a vitrectomy probe in the exemplary embodiment above, the present disclosure is applicable to other ophthalmic or other surgical instruments, each of which may comprise different components therein.

The proximal portion 112 of the probe 110 is partially and longitudinally disposed through the base unit 120 and may be directly or indirectly attached thereto within the interior chamber 124. In one embodiment, the base unit 120 is a handpiece having an outer surface 122 configured to be held by a user, such as a surgeon. For example, the outer surface 122 may be contoured to substantially fit the hand of the user. In one embodiment, the outer surface 122 is textured. In another embodiment, the outer surface 122 is smooth. The base unit 120 may be formed of any suitable materials for surgical procedures. In one embodiment, the base unit 120 is formed of aluminum or stainless steel. In another embodiment, the base unit 120 is formed of a plastic material. Generally, the base unit is preferably formed of any lightweight and durable materials.

The base unit 120 has a proximal end 127 and a distal end 121. The base unit 120 may house at least a portion of an actuating assembly operable to reciprocate the probe 110 within and relative to the base unit 120. The base unit 120 may further provide one or more ports (125, shown in FIGS. 2A and 2B) for one or more supply lines 123 to be routed into the interior chamber 124. For example, the one or more ports (e.g., 125) may provide a connection between the base unit 120 and a vacuum source for aspiration. In another example, the one or more ports (e.g., 125) provides a connection to a pneumatic, hydraulic, or electrical power source to operate the actuating assembly, an illumination device, a laser, or other suitable device within or coupled to the base unit 120.

The instrument 100 further includes a support sleeve 130 slidably coupled to the probe 110 and substantially surrounding at least a portion of the probe 110. Accordingly, the support sleeve 130 has an inner cavity or bore 135 (shown in FIGS. 2A and 2B) through which the probe 110 is disposed. Along with the probe 110, the support sleeve 130 is disposed through an opening of the distal end 121 and partially extends into the interior chamber 124 of the base unit 120. The support sleeve 130 is adjustable relative to the probe 110, enabling a user to slidably position the support sleeve 130 along a longitudinal length L of the probe 110. By re-positioning the support sleeve 130 relative to the distal end 116, the user may selectively adjust the level of support provided to the probe 110. Thus, the rigidity of the probe 110 may be manipulated by a user during use of the instrument 100. For example, protraction of the support sleeve 130 towards the distal end 116 will provide more structural support to the probe 110, thus increasing the rigidity thereof. Conversely, retraction of the support sleeve 130 away from the distal end 116 will decrease the structural support provided to the probe 110, thus decreasing the rigidity thereof.

Generally, the support sleeve 130 may have suitable morphology for providing structural support to the probe 110 during surgical operations. As depicted in FIGS. 2A and 2B, the support sleeve 130 has a proximal end 133 and a distal end 131. In one embodiment, the support sleeve 130 forms an extension of the base unit 120 at the distal end 121. For example, a morphology of the distal end 131 of the support sleeve 130 may conform to a morphology of the distal end 121 of the base unit 120 when in a retracted position. In one embodiment, as depicted in FIGS. 2A and 2B, the distal end 131 of the support sleeve 130 has a conical shape with a cylindrical extension 137 in a distal direction therefrom. The cylindrical extension 137 may have any suitable outer diameter and length to provide additional rigidity or support to the probe 110 as desired while also enabling the support sleeve 130 to be inserted into a cannula during ophthalmic procedures. For example, the cylindrical extension 137 may have a longitudinal length between about 1 millimeter (mm) and about 5 mm, such as between about 2 mm and about 3 mm. In another embodiment, the distal end 131 has a substantially conical shape without a cylindrical extension, and thus forms a nose cone structure together with the distal end 121 of the base unit 120 when in the retracted position. The remainder of the support sleeve 130, including a proximal end 133 thereof, generally has a cylindrical shape. In some embodiments, the support sleeve 130 is substantially cylindrical from the proximal end 133 to the distal end 131.

The inner cavity 135 of the support sleeve 130 is sized to accommodate an outer diameter of the probe 110 while also permitting the support sleeve 130 to be readily actuated along the length L of the probe 110. Thus, an inner diameter of the support sleeve 130 is greater than the outer diameter of the probe 110. Further, the inner diameter of the support sleeve 130 may be uniform throughout the inner cavity 135 to enable unvarying stabilization of the probe 110 throughout the longitudinal entirety of the inner cavity 135.

The proximal end 133 of the support sleeve 130 includes a surface 132 having one or more first features 136 formed thereon. In some embodiments, the surface 132 is an exterior surface of the support sleeve 130, as depicted in FIGS. 1A and 1B. In other embodiments, the surface 132 is an interior surface of the support sleeve 130. The first features 136 may include one or more protrusions, grooves, and/or a spiraling thread formed on the surface 132.

The first features 136 of the surface 132 are operatively mated or engaged with one or more second features 143 formed on a surface 145 of a linear actuator 140 disposed within the interior chamber 124. In the example of FIGS. 2A and 2B, the surface 145 is an interior surface of the linear actuator 140 when the surface 132 is an exterior surface of the support sleeve 130. In another embodiment, however, the surface 145 may be an exterior surface of the linear actuator 140 when the surface 132 is an interior surface of the support sleeve 130. Similar to the first features 136, the one or more second features 143 on the surface 145 may include protrusions, grooves, and/or a spiraling thread. However, at least one of the surface 145 and the surface 132 comprises a spiraling thread formed thereon.

Accordingly, as a result of the engagement of the first features 136 and the second features 143, rotation of the linear actuator 140 about a longitudinal axis X causes linear displacement of the support sleeve 130 in either a first axial direction X1 or a second axial direction X2 along the probe 110. For example, where both the first features 136 and the second features 143 comprise spiraling threads, rotational displacement of the first features 136 causes the first features 136 to slide along the spiraling thread of the second features 143, thereby linearly moving the support sleeve 130. In one embodiment, the linear displacement of the support sleeve 130 is non-rotational. Thus, rotation of the linear actuator 140 causes axial sliding of the support sleeve 130, but not rotational sliding. Rotation of the support sleeve 130 may be prevented by one or more longitudinal ridges, grooves, or stops formed on the support sleeve 130 and mated with one or more longitudinal ridges, grooves, or stops formed on an inner circumferential surface of the opening 119.

The linear actuator 140 is further rotatably coupled to the base unit 120 by a knob 150. In one embodiment, the linear actuator 140 is integrally coupled to the knob 150. That is, the linear actuator 140 and the knob 150 are a single integral component. In other embodiments, the linear actuator 140 and the knob 150 are separate components removably coupled to each other by any suitable coupling mechanism and/or adhesive. For example, the linear actuator 140 and the knob 150 may be snap-fit together. Alternatively, the linear actuator 140 and the knob 150 may be coupled together by a threaded connection.

In one embodiment, as depicted in FIGS. 2A and 2B, the knob 150 is rotatably coupled to the proximal end 127 of the instrument 100 and has the port 125 disposed therethrough. However, it is further contemplated that the knob 150 may be disposed at one of a number of locations along the instrument 100. For example, the knob 150 may be disposed at a more centrally-situated location along a length of the instrument 100, such as the location 129. In a further example, the knob 150 may be disposed adjacent to the distal end 121. In such an example, the knob 150 may be directly coupled to the support sleeve 130 due to the close proximity thereto.

Figure 3A:
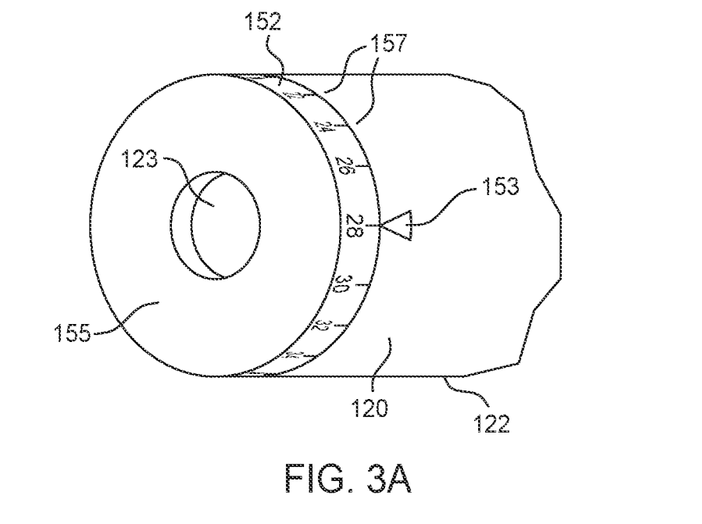
FIG. 3A illustrates a perspective view of a component of the instrument of FIG. 1 according to one embodiment of the present disclosure.
Figure 3B:
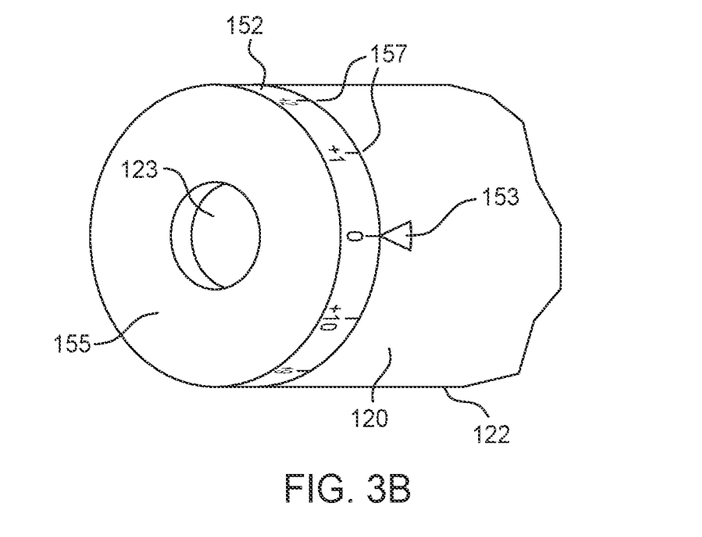
FIG. 3B illustrates a perspective view of a component of the instrument of FIG. 1 according to one embodiment of the present disclosure.
Figure 3C:
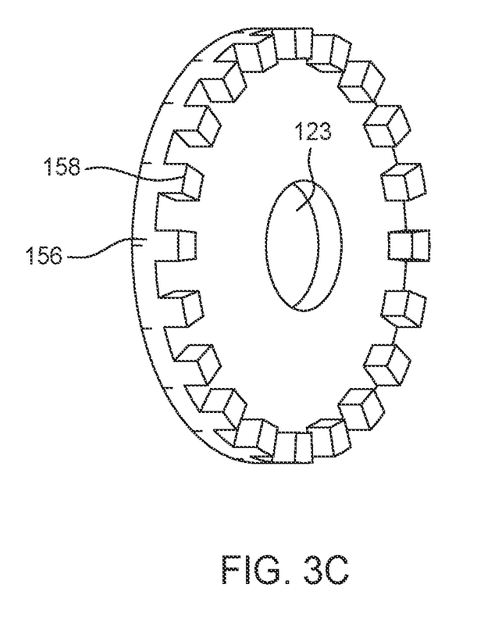
FIG. 3C illustrates a perspective view of a component of the instrument of FIG. 1 according to one embodiment of the present disclosure.

The knob 150 is configured to be gripped and rotated by a user to actuate the support sleeve 130 along the length L of the probe 110. Generally, the knob 150 includes an outer circumferential surface 151. In one embodiment, the outer circumferential surface 151 is textured and/or contoured. In one embodiment, the outer circumferential surface 151 is smooth. In yet another embodiment, the outer circumferential surface 151 includes a dial 152 having a series of markings printed or engraved thereon, as depicted in FIGS. 3A and 3B and described below. The knob 150 may be further configured to rotate about the longitudinal axis X in a locking or non-locking fashion. For example, as depicted in FIG. 3C and described below, the knob 150 may include a locking mechanism having plurality of protrusions or grooves corresponding to one or more protrusions or grooves in the base unit 120 for setting the knob 150 at a preset rotational position. In another example, the locking assembly may include a latch or pawl to lock the knob 150 in a desired rotational position.

In some embodiments, the instrument 100 may further include an integrated micrometer in addition to the knob 150 for accurate measuring of the displacement of the support sleeve 130. For example, the instrument 100 may include a depth micrometer having a dial or face disposed adjacent to the knob 150.

Figure 3D:
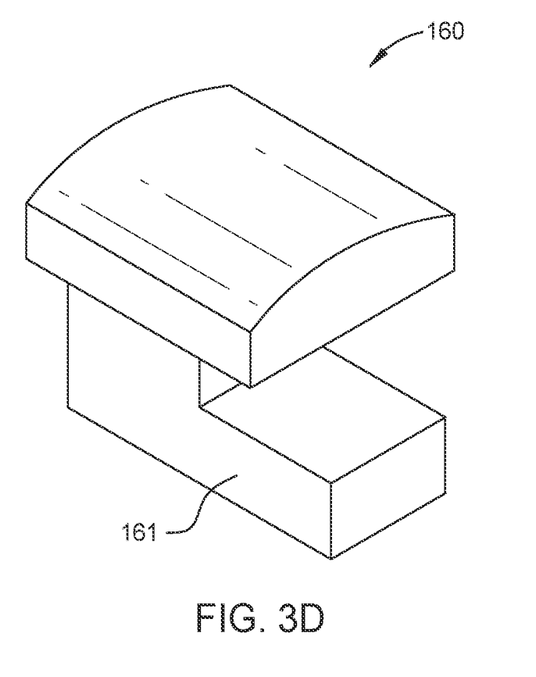
FIG. 3D illustrates a perspective view of a component of the instrument of FIG. 1 according to one embodiment of the present disclosure.

FIGS. 3A, 3B, and 3C illustrate opposing perspective views of an exemplary knob 150 that may be utilized with the instrument 100 according to one embodiment described herein. FIG. 3D illustrates a perspective view of an exemplary latch member 160 that may be utilized with the knob 150 according to one embodiment described herein. Accordingly, FIGS. 3A, 3B, 3C, and 3D are herein described together for clarity.

In one embodiment, the knob 150 includes a dial 152 having a series of markings 157 corresponding to preset linear positions of the support sleeve 130 along the length L of the probe 110. For example, as depicted in FIG. 3A, the dial 152 may include a series of numbers and/or hash marks 157 representing a range of predetermined sizes (e.g., diameters, depths, etc.) of an eye and corresponding to incrementally-preset linear positions of the support sleeve 130 along the length L optimal for each represented eye depth. For example, the markings 157 may represent a range of diameters of the eye and may include increments between 10 mm and 35 mm, such as increments between 10 mm and 30 mm. In another example depicted in FIG. 3B, the dial 152 includes a series of nominal numbers (e.g., +1, +2 . . . +9, +10, etc.) and/or hash marks 157 corresponding to incrementally-preset linear positions of the support sleeve 130 along the length L. In some embodiments, the size of the eye may be measured before or during the surgery (e.g., with diagnostics equipment) and the measurement may be used by the surgeon to set the dial for an appropriate support sleeve position. An adjacent component of the instrument 100, such as the base unit 120, may include a setting marker 153 to indicate a currently selected preset position of the support sleeve 130. Thus, a user can select a desired preset position of the support sleeve 130 by rotating the knob 150 to align the setting marker 153 with the marking 157 corresponding to said desired preset position. Accordingly, rotation of the knob 150 will cause linear displacement of the support sleeve 130 along the length L of the probe 110 to the preset position, thereby adjusting the stiffness of the probe 110 to an optimal level based on the selected preset position. In some embodiments, the markings 157 may be fluorescent (e.g., printed with fluorescent paint) such that the markings 157 are visible to the user in low light conditions.

In one embodiment, the dial 152 is disposed on an outer circumferential surface 151 of the knob 150, as depicted in FIG. 2A. However, it is further contemplated that the dial 152 may be disposed on other surfaces of the knob 150, such as the face 155. For example, the dial 152 may be disposed adjacent the circumferential edge of the face 155 when the knob 150 is disposed at the proximal end 127 of the base unit 120.

The knob 150 may further include a locking mechanism 156 to enable locking rotation of the knob 150. For example, the locking mechanism 156 is utilized to lock the knob 150 at a user-selected preset rotational setting. In one embodiment, the locking mechanism 156 includes a plurality of circumferential features 158 directly or indirectly coupled to the knob 150. The plurality of circumferential features 158 may include axially aligned and circumferential grooves or forwardly-projecting protrusions, as shown in FIG. 3B. In one embodiment, the circumferential features 158 correspond to a matching plurality of features formed on the base unit 120 or other adjacent component of the instrument 100. For example, the circumferential features 158 may form a tongue and groove type locking mechanism with matching features on the adjacent component.

Upon rotation of the knob 150 to a desired rotational position, the circumferential features 158 may engage with the plurality of matching features, thereby locking the knob 150 in place. In such an example, the knob 150 may be biased by a biasing device in a direction along the longitudinal axis (e.g., a distal direction) to enable engagement of the circumferential features 158 with the matching features of the adjacent component. Thus, rotation of the knob 150 may involve slight axial displacement of the knob 150 along the longitudinal axis X to enable the circumferential features 158 to be passed over the matching features during rotation. Accordingly, the user may rotate the knob 150 to a desired position and secure the knob 150 therein automatically. In some embodiments, the knob 150 may click as the circumferential features 158 are engaged with the matching features during rotation of the knob 150, thus audibly alerting the user that a predetermined positional setting of the support sleeve 130 has been reached.

In another embodiment, the locking mechanism 156 further includes a latch member 160, depicted in FIG. 3D. The latch member 160 may be disposed in the outer surface 122 of the base unit 120, the latch member 160 being movable between a locking position in which the latch arm 161 engages between the circumferential features 158 of the locking mechanism 156 and an open position in which the latch arm 161 disengages with the circumferential features 158. The latch member 160 may be biased towards the locking position, thus requiring actuation by the user to move the latch member 160 to the open position. As a result, the user does not have to provide continuous pressure on the latch member 160 in order to lock the knob 150 in place. Although one embodiment of the latch member 160 is depicted in FIG. 3D, the latch member 160 may have any suitable morphology and/or mechanism of action. For example, the latch member 160 may comprise a pawl, a fulcrumed lever, a cog, or other suitable devices.

In summary, embodiments of the present disclosure include structures and mechanisms for adjusting the stiffness of microsurgical instruments, such as small-gauge instruments for minimally-invasive ophthalmologic operations. The instruments described above include embodiments wherein a user, such as a surgeon, may adjust the stiffness of the instruments during use thereof. Accordingly, the described embodiments enable a surgeon to provide an optimal level of stiffness to the instrument depending on the size of the patient's eye, thereby increasing the level of control and ease of use for the surgeon on a per-patient basis.

While the foregoing is directed to embodiments of the present disclosure, other and further embodiments of the disclosure may be devised without departing from the basic scope thereof, and the scope thereof is determined by the claims that follow.

What is claimed is:

1. A surgical instrument, comprising:
a base unit configured to be held by a user;
a probe disposed through an opening in a distal end of the base unit and extending therefrom, the probe having a length parallel to a longitudinal axis;
a support sleeve disposed through the opening in the distal end of the base unit and extending therefrom, the support sleeve substantially surrounding and slidably coupled to a portion of the probe;
a linear actuator coupled to the support sleeve within the base unit, the linear actuator configured to linearly displace the support sleeve along the length of the probe; and
a knob coupled to the linear actuator and rotatable about the longitudinal axis, wherein rotation of the knob rotates the linear actuator to linearly displace the support sleeve along the length of the probe;
wherein rotation of the linear actuator causes non-rotational axial displacement of the support sleeve along the length of the probe.

2. The surgical instrument of claim 1, wherein the support sleeve comprises a first surface having one or more first features formed thereon and operatively mated with one or more second features formed on a second surface of the linear actuator, and wherein rotational displacement of the one or more first features relative to the one or more second features causes linear displacement of the support sleeve.

3. The surgical instrument of claim 2, wherein at least one of the one or more first features and the one or more second features comprises a spiraling thread.

4. The surgical instrument of claim 1, wherein the knob is rotatably coupled to a proximal end of the base unit.

5. The surgical instrument of claim 1, wherein the knob further comprises a dial having a series of markings representing predetermined eye sizes.

6. The surgical instrument of claim 5, wherein the series of markings further correspond to preset positions of the support sleeve along the length of the probe.

7. The surgical instrument of claim 6, wherein rotating the knob to a marking of the series of markings will adjust a stiffness of the probe to a desired level optimal for the predetermined eye size represented by the marking of the series of markings.

8. The surgical instrument of claim 7, wherein the eye size is determined before a surgery and used by the user to set the dial to the desired stiffness level corresponding to the predetermined eye size.

9. The surgical instrument of claim 7, wherein the series of markings are disposed on a circumferential outer surface of the knob.

10. The surgical instrument of claim 9, wherein the series of markings are disposed adjacent a circumferential edge of a face of the knob.

11. The surgical instrument of claim 1, further comprising a locking mechanism coupled to the knob to lock the knob at a preset rotational setting.

12. The surgical instrument of claim 11, wherein the locking mechanism comprises a plurality of axially-aligned circumferential features formed on the knob and corresponding a plurality of matching features on the base unit, the plurality of circumferential features engaged with the matching features when in a locked position.

13. The surgical instrument of claim 11, wherein the locking mechanism comprises a latch member movable between an open and a locking position.

14. The surgical instrument of claim 10, wherein the latch member is a fulcrumed lever.

\* \* \* \* \*